(12) United States Patent
Guire et al.

(10) Patent No.: US 8,936,907 B2
(45) Date of Patent: Jan. 20, 2015

(54) NEURAL TRANSFECTION REAGENTS

(75) Inventors: Eric Guire, St. Paul, MN (US); Jie Wen, St. Johns, FL (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 0 days.

(21) Appl. No.: 13/984,066

(22) PCT Filed: Feb. 7, 2012

(86) PCT No.: PCT/US2012/024085
§ 371 (c)(1),
(2), (4) Date: Aug. 7, 2013

(87) PCT Pub. No.: WO2012/109199
PCT Pub. Date: Aug. 16, 2012

(65) Prior Publication Data
US 2013/0317086 A1    Nov. 28, 2013

Related U.S. Application Data

(60) Provisional application No. 61/440,387, filed on Feb. 7, 2011.

(51) Int. Cl.
| | |
|---|---|
| *C12Q 1/68* | (2006.01) |
| *A61K 47/32* | (2006.01) |
| *C12N 15/87* | (2006.01) |
| *A61K 31/7088* | (2006.01) |
| *A61K 48/00* | (2006.01) |

(52) U.S. Cl.
CPC ............. *A61K 47/32* (2013.01); *C12N 15/87* (2013.01); *A61K 31/7088* (2013.01); *A61K 48/0075* (2013.01); *C12N 2810/65* (2013.01)
USPC ................................ 435/6; 435/325; 435/375

(58) Field of Classification Search
None
See application file for complete search history.

(56) References Cited

U.S. PATENT DOCUMENTS

| | | | |
|---|---|---|---|
| 6,846,809 B2 | 1/2005 | Christiano et al. | |
| 7,045,356 B2 * | 5/2006 | Trubetskoy et al. | 435/458 |
| 7,396,919 B1 * | 7/2008 | Wolff et al. | 536/23.1 |
| 2009/0004118 A1 * | 1/2009 | Nie et al. | 424/9.35 |
| 2010/0166829 A1 | 7/2010 | Slager et al. | |
| 2010/0227798 A1 * | 9/2010 | Robillard et al. | 514/8 |
| 2010/0260846 A1 | 10/2010 | McGonigle et al. | |

OTHER PUBLICATIONS

Chavany et al. (Pharmaceutical Research 1992, vol. 9: 441-449).*
Juliano et al. (Nucleic Acid Research 2008, vol. 36:4158-4171).*
Godeau et al. (J. Med. Chem 2008, 51: 4374-4376).*
Bharali et al., "Organically modified silica nanoparticles: A nonviral vector for in vivo gene delivery and expression in the brain," *PNAS*, Aug. 9, 2005;102(32):11539-11544.
Goldbaum, Ellen, "Using nanoparticles, in vivo gene therapy activates brain stem cells," Medical New Today, Jul. 26, 2005; Retrieved from the Internet:<URL:http://www.medicalnewstoday.com/articles/28052.php>; 4 pgs.
International Search Report and Written Opinion, mailed Mar. 23, 2012, Patent Application No. PCT/US2012/024085, 8 pgs.
Jiang et al., "DNA loaded carrier preferential extravasation from tumor blood vessel," *Int. J. Pharma.*, 2009;369:155-161.
Karra et al., "Transfection Techniques for Neuronal Cells," *J. Neuroscience*, May 5, 2010;30(18):6171-6177.
Katz et al., "Green Fluorescent Latex Microspheres: A New Retrograde Tracer," *Neuroscience*; 1990;34(2):511-520.
Katz et al., "Fluorescent latex microspheres as a retrograde neuronal marker for in vivo and in vitro studies of visual cortex," *Nature*, Aug. 1984;310:498-500.
Oztas, Emin, "Neuronal tracing," *Neuroanatomy*, 2003;2:2-5.
Lehmusvaara et al., "Utility of cell-permeable peptides for enhancement of virus-mediated gene transfer to human tumor cells," *BioTechniques*, 2006;40(5):573-576.
Roy et al., "Optical tracking of organically modified silica nanoparticles as DNA carriers: A nonviral, nanomedicine approach for gene delivery," *PNAS*, Jan. 11, 2005;102(2):279-284.
Sheehan et al., "A horseradish peroxidase-light and electron microscopic study of immunoliposomes utilized for intracellular delivery to the rat striatum," *Neuroscience Letters*, 2002;333:212-216.
Troiber et al., "Nucleic Acid Carriers Based on Precise Polymer Conjugates," *Bioconjugate Chem.*, 2011;22:1737-1752.
Trubetskoy et al., "Recharging cationic DNA complexes with highly charged polyanions for in vitro and in vivo gene delivery," *Gene Therapy*, 2003;10:261-271.

* cited by examiner

*Primary Examiner* — Kimberly Chong
(74) *Attorney, Agent, or Firm* — Weaver Legal and Consulting LLC; Karrie G. Weaver

(57) ABSTRACT

The invention is directed to transfection reagents for the delivery of nucleic acids into neural cells, compositions including the reagents, methods of preparation of such reagents, methods of transfecting cells with such reagents, and uses thereof. In preferred embodiments the reagents comprise horseradish peroxidase and/or a polycarboxylic acid such as poly(acrylic acid) or poly(methacrylic acid).

16 Claims, 3 Drawing Sheets

A.

B.

C.

D.

A.

B.

NEURAL TRANSFECTION REAGENTS

CROSS REFERENCE TO RELATED APPLICATIONS

This application is a U.S. National Stage Application of International Application No. PCT/US2012/024085, titled NEURAL TRANSFECTION REAGENTS, filed on Feb. 7, 2012 claims benefit under 35 U.S.C. §119(e) to U.S. Patent Application Ser. No. 61/440,387, entitled "NEURAL, TRANSFECTION REAGENTS," filed Feb. 7, 2011, the contents of which are incorporated herein in their entirety for all purposes.

GOVERNMENT FUNDING

This invention was made with government support under 1R43MH088092-01A1 awarded by the National Institutes of Health (NIH/NIMH). The government has certain rights in the invention.

FIELD OF THE INVENTION

Inventive concepts relate generally to the field of nucleic acid transfection. Reagents useful for transfection of neuronal cells, as well as related compositions and methods are described.

BACKGROUND

Generally speaking, transfection is understood as involving the introduction of a foreign material (such as nucleic acid or proteins) into a cell. Transfection as discussed herein involves introduction of nucleic acid into a cell.

Delivery of nucleic acid to cells is a powerful tool for study and treatment of various medical conditions, as well as a basic research tool. General methods for introducing nucleic acids into mammalian cells include chemically-mediated transfection (such as calcium phosphate), lipid-mediated transfection (such as Lipofectamine™), transfection via cationic polymers (such as poly(ethyleneimine) (PEI) and poly-L-lysine (PLL)), instrument-mediated transfection (for example, using such known devices as Electroporator, Nucleofector®, and Gene Gun), magnetofection, and viral transduction. Of these methods, transfection reagents employing chemicals, lipids, polymers, or combinations thereof that can efficiently deliver nucleic acids to cells offer the greatest convenience while avoiding the risks, toxicity, and regulations associated with the use of viruses, as well as the physical cellular trauma associated with the use of ballistic or electroporation techniques.

Cationic polymers such as PEI and PLL have become commercially available for transfection of mammalian cells. These positively charged polymers are efficient at forming polyplex nanoparticle complexes with negatively charged nucleic acids, including plasmid DNA and siRNA. More recent PEI formulations have in many instances been found to be less toxic and more efficient than lipid-based transfection reagents. Amine-rich polymers such as PEI (mixture of primary, secondary, and tertiary amines) facilitate endosomal escape through the so-called proton-sponge effect, whereby amine buffering of protons pumped into endosomal compartments during acidification causes their swelling and rupture, releasing the carrier and nucleic acid(s) into the cytoplasm within about four hours. This mechanism may be primarily responsible for more efficient transfection of mammalian cells by PEI-based vectors when compared to cationic lipid-based vectors.

Delivery of nucleic acid to neuronal cells is critical for the study and understanding of neuronal cell function in both healthy and disease states. However, transfection of developmentally mature cultured neurons (greater than approximately 9 days in vitro), as well in vivo neuronal transfection, present special challenges. Non-viral transfection reagents for the delivery of nucleic acids to neurons or neural circuits in vivo, or to mature neurons in vitro, are notably inefficient. Thus, reagent-based methods for the genetic manipulation of neurons are typically limited in use to developmentally immature cultured neurons.

Difficulties in transfecting developmentally mature neurons can be illustrated by work done with some common transfection reagents. For in vitro use, commercially available transfection reagents such as calcium phosphate and cationic lipids (such as Lipofectamine 2000™) have been the state of the art for many years, achieving transfection rates of greater than 50% in various non-neuronal mammalian cells, for example HEK-293 and fibroblasts. These transfection reagents are also used with fair success in dissociated early-postnatal or embryonic primary neuronal cultures when used during the first few days in culture and prior to the development of a mature network of functional synapses (up to approximately 20-25% transfection efficiency). However, these reagents typically produce transfection rates of much less than 5% for developmentally mature neurons in dissociated cultures (greater than 7-14 DIV). This low efficiency transfection of developmentally mature neurons, coupled with inherent serum instability, makes these reagents poorly suited for many, if not most, in vivo applications. This shortcoming has in turn curtailed the application of powerful molecular genetic tools in neuroscience research beyond their application to developmentally immature dissociated cultures.

Moreover, a common observation in the field is that lipid-transfected neurons in vitro present challenges in electrophysiological procedures, due to increased membrane fragility and leak currents, and a trend towards depolarized resting potentials when compared to untransfected cells. This observation suggests that these reagents posses an inherent toxicity to neurons.

In further studies, it has been demonstrated that the efficiency of PEI- and PLL-mediated transfection in mature cultured neurons is stubbornly low. Accordingly, these techniques have found limited utility as a neuronal transfection reagent either in vitro or in the more challenging environment of the central nervous system (CNS). Indeed, one effort found that laser-induced stress waves were required for efficient transfection with a PEI gene carrier in mouse CNS. Other studies have shown that differentiation of neurotypic cells results in markedly decreased uptake of transfection reagents. It appears likely that mature neurons are fundamentally resistant to transfection with cationic reagents, because these reagents do not cross the neuronal plasma membrane efficiently on their own.

In general, there are a number of barriers for transfection-based delivery of nucleic acids to mammalian cells in vivo, including, for example: nucleic acid particle stability in the presence of serum proteins, protection from nucleases and acid hydrolysis, nucleic acid particle interaction with plasma membrane, nucleic acid particle internalization, escape from endocytic vesicles, efficient nucleic acid dissociation, and acute or chronic toxicity.

In addition to the above-mentioned barriers encountered in delivery of nucleic acid to mammalian cells, neurons present further challenges to transfection techniques. Developmentally mature neurons appear to have unique requirements for the internalization of nanoparticles, with cationic substances generally performing poorly. The unique characteristics and composition of mature neuronal plasma membrane lipids, associated membrane proteins, and variations in the structure and sulfonation of extracellular glycoseaminoglycans such as heparin sulfate (which is known to be cell type dependent) may decrease the binding affinity/avidity or uptake of conventional non-viral gene vectors by mature neurons. These barriers to non-viral gene transfer, especially in mature neurons, are a major bottleneck as the efficiency of the gene expression in vivo often lies below the threshold efficiency for functional or therapeutic changes. Further, for delivery of nucleic acids to neuronal soma, the ability for the vector to undergo retrograde transport could be a significant advantage, given the unique, highly elongated and branched morphology typical of mature neurons, and the relative scarcity of neuronal soma versus neurophil in brain parenchyma. However, this intracellular transport may present further challenges, as it involves further targeting of the nucleic acid even after it has been taken up into a neuronal cell.

On a separate subject, neuroanatomical tract-tracing involves methods to label and follow the course of neural pathways by axonal transport of injected neuronal tract-tracers. Neuronal tract-tracing materials generally comprise markers that can be stained or fluoresce, to enable their visualization. Neural tract-tracing can be retrograde or antero-grade. Negatively charged tract-tracers are not, on their own, considered suitable nucleic acid carriers because they have not been found to efficiently condense nucleic acids.

Agents capable of condensing and maintaining nucleic acids in a form suitable for transfection under physiological conditions are generally cationic. Such agents commonly used for the condensation of nucleic acids in vitro include multivalent cations, basic proteins or peptides, cationic polymers and copolymers (polycations), cationic liposomes, or combinations thereof. Cationic carriers may also include suspensions of suitable sized nanoparticles bearing a high density of cationic charges on their surface and which are capable of forming a complex with nucleic acids that is stable under physiological conditions.

SUMMARY OF THE INVENTION

In a first general aspect, transfection reagents are described for delivering nucleic acid to target cells, in particular, neurons. Also described are transfection compositions, as well as methods of preparing and methods of using such transfection reagents to deliver nucleic acid to target cells, such as neuronal cells or neurons.

Transfection reagents are described that comprise at least two main components, namely, a neural transport agent and a nucleic acid carrier disposed within the neural transport agent. Accordingly, the neural transport agent presents a surface chemistry that can target and deliver the transfection reagents to a desired cell population, such as neuronal cells. The nucleic acid carrier disposed within the neural transport agent can provide significant advantages over many prior approaches to nucleic acid transfection of neurons.

In some embodiments, the transfection reagents can comprise at least one additional component, such as, for example, a passivation polymer, an endosome lysis agent, a linker, a proteinaceous compound, a lipid, a pharmaceutically acceptable carrier, additional targeting moieties, or any combination of such components.

Transfection compositions (such as kits), as well as methods of using the transfection reagents to deliver nucleic acid to neuronal cells are also described. Further embodiments will be apparent upon review of the disclosure.

In one aspect, inventive concepts provide transfection reagents comprising: (a) a neural transport agent, and (b) a nucleic acid carrier disposed within the neural transport agent, wherein the neural transport agent comprises an enzyme, polymer, lectin, fluorescent dye, dextran, or a combination of any two or more of these, and wherein the neural transport agent has a net negative charge under mammalian physiological conditions.

The neural transport agent can comprise a polycarboxylic acid.

The neural transport agent can comprise an acrylic polymer. In some embodiments, the acrylic polymer can comprise poly(acrylic acid) or poly(methacrylic acid).

The neural transport agent can comprise horseradish peroxidase.

The nucleic acid carrier can contain amines.

In some embodiments, the nucleic acid carrier and the neural transport agent contain complementary reactive groups. The nucleic acid carrier and the neural transport agent can contain complementary bioorthagonal chemically reactive groups.

The nucleic acid carrier and the neural transport agent can be joined by complementary ligands.

In some embodiments, the nucleic acid carrier comprises a non-viral carrier.

Optionally, the transfection reagent additionally comprises a neuronal cell subtype targeting ligand.

In some aspects, the nucleic acid carrier can be a nanoparticle whose diameter is in a range of 5 nm to 250 nm. The transfection reagent can further comprise a nucleic acid.

In some aspects, the nucleic acid carrier comprises a polyplex forming agent. In accordance with inventive aspects, the transfection reagent can further include a nucleic acid, and the polyplex forming agent and the nucleic acid can form a condensed particle whose diameter is in a range of 5 nm to 250 nm.

In some embodiments, the nucleic acid carrier comprises a cationic polymer.

The nucleic acid carrier can comprise an acrylic ester polymer.

The transfection reagent can further comprise nucleic acid. In some aspects, the nucleic acid can be selected from RNA, DNA, siRNA, miRNA, piRNA, shRNA, antisense nucleic acid, aptamers, ribozymes, locked nucleic acid, catalytic DNA, plasmid, cosmid, artificial chromosomes, morpholinos or other synthetic nucleic acid analogs.

Optionally, the transfection reagent can further comprise a passivating polymer. In some aspects, the nucleic acid carrier or passivating polymer contains amines.

Inventive concepts further include compositions (for example, kits) for transfection of neurons. In some aspects, such compositions comprise a neural transport agent and a nucleic acid carrier, wherein the neural transport agent comprises an enzyme, polymer, lectin, fluorescent dye, dextran, or a combination of any two or more of these, and wherein the neural transport agent has a net negative charge under mammalian physiological conditions. Optionally, the compositions can include nucleic acid. Optionally, the neural transport agent and the nucleic acid carrier can be separate components of the compositions, but capable of forming a stable interaction when mixed together. Separate components can be provided as solutions or lyophilized.

In still further aspects, inventive concepts provide methods for preparing a transfection reagent, the method comprising a step of combining a neural transport agent and a nucleic acid carrier in a manner such that the nucleic acid carrier is disposed within the neural transport agent. The neural transport agent can comprise an enzyme, polymer, lectin, fluorescent dye, dextran, or a combination of any two or more of these, and wherein the neural transport agent has a net negative charge under mammalian physiological conditions. In accordance with these aspects, the nucleic acid carrier can comprise a nanoparticle or a polyplex forming agent. In some embodiments, the methods can further comprise the step of condensing nucleic acid with or onto the carrier material. In some embodiments, condensation can be performed prior to the step of combining the neural transport agent and nucleic acid carrier.

DETAILED DESCRIPTION

Figure 1:
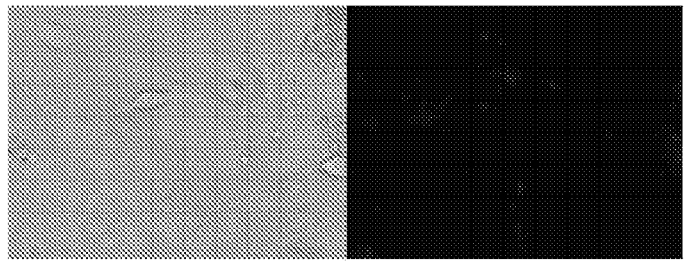
FIG. 1 illustrates brightfield image and corresponding fluorescence image of mature cultured neurons including cationic nanoparticle/polyacrylic acid conjugates introduced into mature neurons in accordance with inventive aspects.
Figure 1:
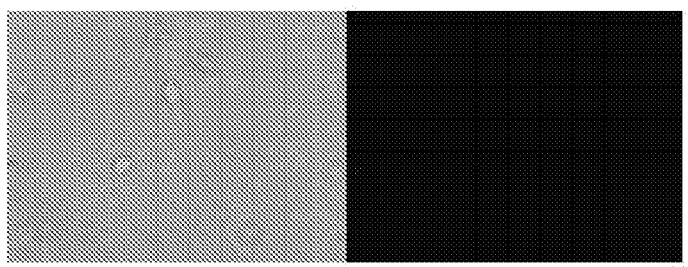
Figure 1:
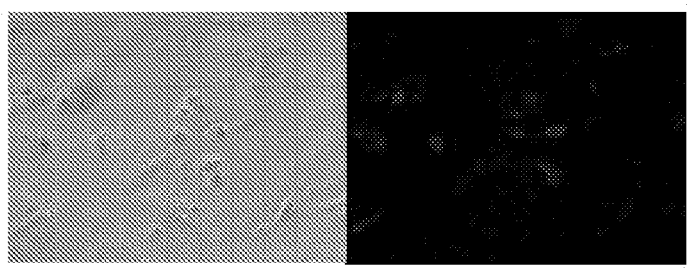
Figure 1:
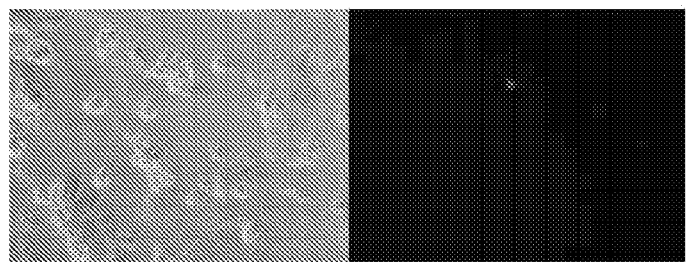

The embodiments of the present invention described herein are not intended to be exhaustive or to limit the invention to the precise forms disclosed. Rather, the embodiments are chosen and described so that others skilled in the art can appreciate and understand the principles and practices of the present invention. This application is intended to cover adaptations or variations of the present subject matter.

All publications and patents mentioned herein are hereby incorporated by reference to the same extent as if each individual publication or patent application was specifically and individually indicated by reference. The publications and patents disclosed herein are provided solely for their disclosure. Nothing herein is to be construed as an admission that the inventors are not entitled to antedate any publication and/or patent, including any publication and/or patent cited herein.

In the specification and in the claims, the terms "including" and "comprising" are open-ended terms and should be interpreted to mean "including, but not limited to . . . . " These terms are broader than, and therefore encompass, the more restrictive terms "consisting essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

Generally speaking, inventive concepts provide transfection reagents comprising a neural transport agent, and a nucleic acid carrier disposed within the neural transport agent. In some aspects, there are provided transfection reagents that can utilize features of selected soluble, net-negative neural transport agents to target specific cells. By providing a nucleic acid carrier within the neural transport agent, the carrier can be more efficiently endocytosed by neuronal cells and, if so designed, transported axonally. In some aspects, inventive transfection reagents can be used to transfect neurons in a targeted manner. For example, principal neurons having projections to a depot of transfection reagent, as wells as neurons located in the vicinity of the transfection reagent depot, can be targeted for transfection by virtue of a neural transport agent. Inventive transfection reagents can also be used for global transfection of neuronal cells, for example by suspension of the reagent in cell culture media, intraventricular or intrathecal injection.

Inventive concepts can be viewed as employing a "Trojan horse" approach, wherein a nucleic acid carrier complex is presented to cells disguised with a surface chemistry that effectively masks the DNA/carrier complex. Inventive concepts can be seen as providing foremost the uptake, but also (when desired) the intracellular transport of nucleic acid complexes within mature neurons. To illustrate these concepts, one useful embodiment can be illustrated as follows: cationic amine nucleic acid carriers are synthesized and complexed with nucleic acid. The nanoparticulate complex is then conjugated to polyacrylic acid (PAA) and/or other neural targeting and/or transport surface chemistries and used to transfect mature neurons in vivo or in vitro. When presented to neuronal cells, the surface chemistry (here PAA or other neural transport agent) is recognized by the cells, and the transfection reagent is taken up into the cell. Subsequently, the nucleic acid can be released from the nucleic acid carrier (here cationic amine carrier) within the neuronal cell, where it can provide its intended function.

If desired, inventive reagents can provide the ability to transport nucleic acid within axons or dendrites, thereby delivering nucleic acid to an intracellular target site. With regard to the direction of transport, one can distinguish between anterograde and retrograde transportation of transfected material. Retrograde transport generally refers to transportation towards the soma. Anterograde transport generally refers to transportation away from the soma, towards axons or dendrites. In some aspects, inventive reagents include neural transport agents that are retrograde transporters. In these aspects, nucleic acid can be delivered toward the cell soma, such as may be desired for the transcription of DNA constructs into RNA. It is also recognized that neural transport agents include anterograde transporters, and inventive concepts extend to a nucleic acid carrier disposed within such material. In accordance with these aspects, nucleic acid can be delivered toward axons or dendrites.

In some embodiments, intracellular transport of the carrier is not seen as an essential component. An illustrative example is the transfection of neurons with interfering RNA directed against mRNA's located in the vicinity of dendritic and axonal synapses. Such localization may be considered either presynaptic or postsynaptic in nature.

Optionally, and as discussed in more detail elsewhere herein, inventive transfection reagents can include additional components, such as a passivating polymer. In some aspects, the passivating polymer can be included at a position between the nucleic acid carrier and the neural transport agent.

The word "cell" is used herein in its usual biological sense, and does not refer to an entire multicellular organism. The cell may be present in an organism which may be a human but is preferably of animal origin, for example, such as humans, cows, sheep, apes, monkeys, swine, dogs, cats, rodents, birds, fish, reptiles, insects, and the like. Notwithstanding the foregoing, several steps of producing nucleic acid suitable for use in accordance with inventive concepts (such as small interfering RNA) may require use of prokaryotic cells (for example, bacterial cells) or eukaryotic cells (for example, mammalian cells) and thereby are also included within the term "cell."

Inventive transfection reagents are useful for transfecting mammalian cells, and in particular, neuronal cells, including developmentally mature neurons. In some aspects, inventive transfection reagents can find particular utility in delivery of nucleic acid to mature neurons. Throughout this disclosure, the terms "neuronal cells" and "neurons" may be used interchangeably without intending to imply any distinction between these specific terms. The phrase "developmentally mature neuron" refers to a terminally differentiated neuron having synaptic connections with other cells or that exists in a functional synaptic network.

As used herein, a "polymer" is a molecule of high relative molecular mass, the structure of which essentially comprises the multiple repetitions of units derived from molecules of low relative molecular mass. Unless otherwise stated, polymers include natural (such as proteins, peptides, polysaccharides, nucleic acid, oligomers, and the like), and synthetic materials. In many cases, especially for synthetic polymers, a molecule can be regarded as having a high relative molecular mass if the addition or removal of one or a few of the unit has a negligible effect on the molecular properties. It is however recognized that in some cases, and in particular for proteins and nucleic acids, removal of one or a few of the units can drastically alter biochemical function of the polymer without drastically altering the molecular properties such as mass, size or solubility. Thus, the above description for determining relative molecular mass is inapplicable in these cases.

As used herein, the term "complex" refers to a chemical association of two or more chemical species through non-covalent bonds.

Generally speaking, transfection reagents are described herein that are platform based and comprise a nucleic acid carrier, chemically masked for neuronal delivery and uptake through surface modification. This structural feature can be derived through sequential steps or self assembly. Neural targeting/transport surface chemistry can provide efficient transfection reagent uptake and, in some aspects, axonal or dendritic transport. One of skill in the art will readily appreciate that axonal or dendritic transport of a nucleic acid payload is not necessarily a required feature for transfection, for example, when nucleic acid can provide an intended effect without transport to the soma, or without transport towards the distal ends of axons or dendrites. In some embodiments, retrograde transport can be particularly important for transfection of mature neurons with gene constructs requiring nuclear transcription, due to the highly elongated nature of neuronal processes (and consequently, the extensive surface area of plasma membrane present in the neuron that is relatively far away from the soma).

Optionally, the transfection reagents can include surface functional groups for customizable attachment of targeting ligands. When included, such target ligand attachment may provide neuronal sub-type targeting capability. Inventive transfection reagents can therefore provide customizable nucleic acid loading and surface conjugation or co-conjugation of targeting moieties by an end user. In these aspects, transfection reagents can be provided that comprise a neural transport agent and a nucleic acid carrier disposed within the neural transport agent. Alternatively, the nucleic acid carrier can be provided separately and joined to the neural transport agent following complexation with nucleic acids. An end user can load a desired nucleic acid into the carrier portion of the transfection reagent. Functional groups present at an outer surface portion of the transfection reagent can provide sites for coupling of neural transport agent by an end user, and optionally provide sites for coupling of desired targeting ligands as well.

In some aspects, inventive transfection reagents can provide novel nucleic acid delivery compositions that are simple to construct, well-suited for scale-up, and easily manipulated for targeting. In some aspects, inventive transfection reagents can provide enhanced neuronal cell transfection with genetic constructs in formulations having low or reduced cytotoxicity.

Inventive transfection reagents can provide one or more additional benefits as well.

A nucleic acid component of the transfection reagent can be more robust and less subject to degradation during subsequent processing and/or use when disposed within a neural transport agent. The nucleic acid interacts with a nucleic acid carrier, thereby forming a nucleic acid/carrier complex (also referred to herein as a "nucleic acid complex" or "carrier/cargo complex"). The nucleic acid carrier within the transfection reagent is selected to interact with a nucleic acid, such that the nucleic acid is stably held within the transfection reagent and delivered to a target cell. The nucleic acids that are carried by inventive transfection reagents can retain their activity and can be used successfully to transfect target neuronal cells.

In some embodiments, components of the transfection reagent can be selected to be cleared from the body with time, for example, when components are degradable and/or capable of being excreted from the body. An illustrative embodiment of this feature is a transfection reagent comprising low molecular weight polyacrylic acid as neural transport agent, a polycyanoacrylate as nucleic acid carrier, and low molecular weight polyethylene glycol (PEG) as passivation polymer. In this embodiment, polycyanoacrylate is biodegradable, while low molecular weight PEG and polyacrylic acid can be excreted from the body.

Transfection reagents in accordance with inventive principles can enable the targeted regulation and observation of neuroplasticity and circuit function in the intact nervous system using molecular constructs. In addition, inventive transfection reagents can provide therapeutic treatments for a variety of neurological diseases and disorders, including but not limited to, Parkinson's disease, brain injury, post-traumatic stress disorder, and chronic drug addiction. Such neurological diseases or disorders may be manifest in the peripheral or central nervous systems.

Optionally, transfection reagents can be provided that do not include viral components. In these aspects, inventive concepts can provide non-viral transfection reagents. For example, the nucleic acid carrier can comprise a non-viral carrier. Such non-viral embodiments can, in some embodiments, provide reduced immunogenic potential, reduced mutagenic risk, and easier handling and manufacturing when compared to viral based transfection systems.

In some aspects, transfection reagents in accordance with inventive principles can, in some embodiments, reduce or avoid risks associated with use of bacterial toxins (or portions of bacterial toxins). For example, while portions of bacterial toxins could be considered non-toxic, these fragments may still be immunogenic. Therefore, it can be advantageous to avoid use of bacterial toxins or fragments of these toxins, to thereby reduce risk of immunogenic effects when administered to a patient.

Various features of inventive transfection reagents will now be described in more detail.

Transfection reagents in accordance with inventive principles include at least two main components, namely, a neural transport agent and a nucleic acid carrier disposed within the neural transport agent. Features of suitable neural transport agents will now be described.

In accordance with inventive concepts, neural transport agents such as horseradish peroxidase (HRP), lectins, dextrans, synthetic fluorescent compounds and the like, can be used to provide effective chemistry for both traversing the plasma membrane of developmentally mature neurons and subsequent retrograde or anterograde transport. While not intending to be bound by a particular theory, it is believed these compounds traverse the plasma membrane by inducing local gelation of phospholipid bilayers, creating a local phenomenon reminiscent of lipid rafts. Axons and dendrites are rich in lipid rafts, which are believed to anchor signal transduction complexes and associated endocytic machinery. Furthermore, lipid raft-associated signaling machinery (such as signalosomes) is capable of efficient transport to the nucleus upon endocytosis. Thus, it is believed negatively charged neural transport agents according to inventive concepts may utilize similar physiochemical phenomena to enter neuronal cells. This is distinct from the selective and highly specific receptor-ligand mediated uptake, such as is believed to occur for some known tract-tracers.

Inventive neural transport agents comprise a material capable of traversing the plasma membrane of mature neurons. In accordance with inventive concepts, neural transport agents can include substances that can achieve such function in their isolated form, such as HRP, lectins, dextrans and some synthetic fluorescent compounds. Further, neural transport agents can include substances that induce such behavior in situ (when present within inventive transfection reagents described herein, and when present under physiological conditions).

In some aspects, suitable neural transport agent can provide a net anionic surface chemistry to the overall transfection reagent when the transfection reagent is exposed to normal human or mammalian physiological conditions of cerebrospinal fluid, blood, or plasma (for example, pH in the range of about 7.3 to about 7.4; temperature in the range of about 36° C. to about 39° C.). In accordance with these aspects, neural transport agents include synthetic polymers having a net negative charge, or formulated to carry a net negative charge, under mammalian physiological conditions. Thus, in some embodiments, inventive transfection reagents comprise neural transport agent comprising synthetic polymer having a net negative charge, or formulated to carry a net negative charge, under mammalian physiological conditions, in combination with a nucleic acid carrier.

Thus, in some aspects, neural transport agent can comprise an anionic masking agent. In these aspects, the neural transport agent can provide a net negative overall surface chemistry that can mask the cationic nucleic acid carrier contained within it. The formed transfection reagent can thus transverse the plasma membrane of neuronal cells.

In some preferred aspects, the material comprising the neural transport agent is selected such that it does not interfere with the function and/or interaction of other components of the transfection reagent (and in particular, the nucleic acid carrier and nucleic acid cargo), when the transfection reagent is properly assembled in its usable form. For example, it can be desirable to select a neural transport agent that does not adversely affect release of the nucleic acid once the transfection reagent is inside a neuronal cell. For example, the neural transport agent can be selected to be permeable, such that it does not prevent unpacking and release of nucleic acids within the cell. In other aspects, the neural transport agent can be selected or modified to effectively render it biodegradable or bioerodible, such that nucleic acid can be released from inventive transfection reagents as the neural transport agent (or an optional underlying layer) degrades. In some aspects, the neural transport agent does not interfere with formation and/or maintenance of the nucleic acid carrier/cargo complex.

Optionally, the neural transport agent can be selected to provide transport of the transfection reagent within the neuron (i.e., intracellular transport). In some preferred aspects, inventive transfection reagents can include neural transport agents that achieve retrograde transport within neurons (from the axon or dendrites of a neuron toward the soma). In some aspects, inventive transfection reagents can include neural transport agents that achieve anterograde transport within neurons. In still further aspects, transportation within the neurons is not required.

In some aspects, neural transport agent suitable for incorporation into inventive transfection reagents comprises an enzyme, polymer, lectin, fluorescent dye, dextran, or a combination of any of these. Thus, in some embodiments, the transfection reagents comprise a neural transport agent selected from an enzyme, polymer, lectin, fluorescent dye, or a combination of any of these, wherein the neural transport agent provides a net anionic surface chemistry to the overall transfection reagent when the transfection reagent is exposed to normal human or mammalian physiological conditions of cerebrospinal fluid, blood, or plasma.

Illustrative enzymes include, for example, HRP.

Illustrative polymers include, for example, polycarboxylic acid; acrylic polymer (for example, acrylic esters), such as, for example, polyacrylic acid or polymethacrylic acid; or the like. Another illustrative polymer comprises the anionic material that has been used as a component in the fabrication of fluorescent acrylic latex "microspheres" (which as described are anionic nanospheres, See Katz L C, Burkhalter A, Dreyer W J, Fluorescent latex microspheres as a retrograde neuronal marker for in vivo and in vitro studies of visual cortex, Nature (1984) August 9-15; 310(5977):498-500).

Illustrative lectins include, for example, plant lectins, such as wheat germ agglutinin (WGA), and the like.

Illustrative fluorescent dyes include, for example, Evans Blue (EB), 4'6-diamidino-2-phenylindole (DAPI), lucifer yellow (LY), and the like.

Illustrative dextrans include, for example, water soluble dextran conjugates and derivatives, dextran amines (which may adopt a negative charge in situ by stably binding with negatively charged serum components), and dextran sulfates.

In some embodiments, the neural transport agent comprises a viral protein or peptide sequence. Illustrative viral proteins are those obtained, for example, from such neurotrophic viruses as herpes simplex virus, adeno virus, pseudo rabies, and the like.

In still further embodiments, a neural transport agent may comprise a small, negatively charged molecule that induces or provides a negative net charge on the surface of the transfection reagent when stably bound to the transfection complex, and wherein the addition of the agent can enable the effective transfection of developmentally mature neurons with nucleic acids.

Optionally, the neural transport agent further comprises a neuronal ligand capable of translocation to the nucleus or perinuclear region upon extracellular binding and activation of a receptor. Illustrative ligands in accordance with these aspects include, but are not limited to, brain-derived neurotrophic factor (BDNF), as well as ligands that bind the extracellular portion of G protein-coupled receptors (GPCR), and/or receptor tyrosine kinases (RTK).

Optionally, the transfection reagent can further comprise a neuronal cell subtype targeting ligand. Illustrative targeting ligands include DAMGO peptide, MK-801, fibroblast growth factor (FGF), Estradiol, and philanthotoxin-433. In some aspects, these and other targeting ligands can be considered latent in the sense that cell surface expression and availability of their binding partner(s) may be regulated by neuronal activity, neuronal plasticity, or neuronal damage or ischemia. In some aspects, this additional inclusion of a targeting moiety on the surface of the nucleic acid carrier-neural transport complex can also be an effective means for the selective transfection of a subpopulation of neurons which differentially express a complementary surface marker. Such complementary surface markers include, for example, receptors, epitopes, ligands, or other surface moieties present in sufficient quantities to enable targeting of the complex through a selective chemical interaction with the targeting moiety.

In some embodiments, the neural transport agent comprises a synthetic polymer (that is, a polymer that comprises a man-made sequence). In some aspects, the neural transport agent comprises a negatively charged polymer, as described herein. In some embodiments, the negatively charged polymer can be selected from negatively charged neural tract tracing materials. In some particular embodiments, the neural transport agent comprises a polycarboxylic acid. Illustrative polycarboxylic acids include acrylic polymers having a net negative charge, such as polyacrylic acid or polymethacrylic acid.

The second main component of inventive transfection reagents is a nucleic acid carrier. Features of the nucleic acid carrier will now be described.

In accordance with inventive concepts, nucleic acid carriers are selected to transport nucleic acids to a site of action in a body, and once that site of action is reached, the carriers release the nucleic acids, to achieve a desired effect. Nucleic acid carriers thus complex with a cargo nucleic acid for a period of time, until a desired target site is reached. Interaction between nucleic acid carrier and cargo is therefore stable, but non-permanent.

In accordance with inventive concepts, a nucleic acid carrier is selected to form a complex with its cargo nucleic acid, such that the nucleic acid can enter a neuron without significantly losing its function (for example, by degradation). Once inside a neuron (site of action), the cargo nucleic acid is released from the carrier. Suitable nucleic acid carrier can include those compounds that can be complexed with nucleic acids in order to preserve the activity of the nucleic acids during manufacturing, end user preparation, and/or delivery processes within a patient (to the site of action). Without intending to be bound by a particular theory, it is believed that the complex between the nucleic acid carrier and its cargo nucleic acid provides a compacted, more protected form of the cargo that is more stable during preparation and/or transfection procedures described herein. In some embodiments, the carrier forms a complex with nucleic acid that is also sufficiently stable to undergo extended axonal transport within endosomal compartments (for example, retrograde transport to the soma). Once the site of action is reached, the nucleic acid cargo is released, to achieve its desired effect.

The carrier/cargo complex can form as a result of electrostatic interaction of the carrier with its cargo nucleic acid (such as salt bridges), hydrophobic interaction, van der Waals interaction, hydrogen bond formation, by base pairing, or other complexation, so long as the nucleic acid is stably maintained in association with the nucleic acid carrier until its desired release subsequent to transfection into a neuronal cell. By "stably maintained," the nucleic acid retains the activity it possessed prior to its modification or association with the nucleic acid carrier and delivery to the neuron, such that the nucleic acid can achieve the desired effect at the site of action. In some aspects, carrier-nucleic acid interactions can be primarily based upon the phosphate backbone and are not base sequence-specific.

In some embodiments, the nucleic acid carrier can undergo condensation (for example, electrostatic condensation) with its cargo nucleic acid, to form a carrier/cargo complex.

In preferred aspects, nucleic acid carriers can be stable under extracellular conditions to prevent the release of cargo at off-target sites and protect the nucleic acid from enzymatic degradation.

In some aspects, the nucleic acid carrier can be selected to have an advantageous combination of such properties as biocompatibility, biodegradability, lysosomal buffering features, appropriate size for neuronal cell uptake, and the like. If desired, nucleic acid carrier can comprise a non-viral carrier, for example, when polymeric or nanoparticulate carriers are utilized. In some embodiments, the nucleic acid carrier/cargo complex, once formed, can have an overall diameter suitable for transport across neuronal plasma membrane, for example, about 300 nm or less, or about 250 nm or less, or in a range of about 5 nm to about 250 nm, or about 10 nm to about 200 nm, or about 20 nm to about 200 nm, or about 50 nm to about 200 nm.

The terms "biodegradable" and "biodegradability" as used herein, shall refer to those natural or synthetic polymers that break down under physiological conditions (such as by enzymatic or non-enzymatic processes) into constituent components over a period of time. The terms "erodible," "bioerodible," and "biodegradable" is used herein interchangeably with the term "degradable."

In some aspects, nucleic acid carrier can comprise a cationic material (for example, a material having a net positive charge). The nucleic acid cargo can be packaged into nano-sized structures enabling uptake into cells. When the nucleic acid carrier comprises a polymer, such structures are referred to as polyplexes, and are described in more detail below. Alternatively, nucleic acid carrier can comprise a charge-neutral material. In these embodiments, interaction between the nucleic acid carrier and its cargo can occur through other mechanisms described herein.

In accordance with inventive concepts, the cationic nucleic acid carrier material can be any cationic molecule suitable for binding a nucleic acid. Suitable cationic material comprises cationic polymers, cationic lipids, or combinations thereof.

Illustrative cationic polymers include acrylic polymers and acrylic copolymers. One exemplary acrylic polymer is a multifunctional polycyanoacrylate, modified to contain pendent amines. Such polycyanoacrylate can be synthesized by copolymerization of an allyl cyanoacetate using formaldehyde as a condensation reagent, and subsequently reacting with thiol-containing amines. Other cationic polymers include, but are not limited to, polycation containing polyamines such as polyethylenimines (PEI), polypropylenimine, polyamidoamine (PAMAM) dendrimers, and poly(beta-aminoesters); histones; cationized human serum albumin; and aminopolysaccharides such as chitosan. PEIs can be linear or branched.

Illustrative cationic lipids include, but are not limited to, 3β[N—(N'N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecyenoyl)-3-dimethylammonium-propane (DODAP); 1,2-dilinoleyloxy-3-dimethylaminopropane (Dlin DMA); and derivatives thereof. Other exemplary lipids can include, for example, lipidoids, atuplex formulations, and PEGylated forms of lipids or polymers described above.

In other embodiments, nucleic acid carrier could comprise non-cationic (for example, charge neutral) polymers, lipids, or a combination of two or more of these.

Additional nucleic acid carriers include peptides such as poly-L-lysine, poly-L-ornithine, and poly(4-hydroxy-L-proline) ester. As used herein, the term "peptide" includes any compound containing two or more amino acid residues joined by amide bonds formed from the carboxyl group of one amino acid (residue) and the amino group of the next one. As such, peptides can include oligopeptides, polypeptides, proteins, and the like. Illustrative oligopeptides include, but are not limited to, oligopeptides comprising one or more cationic amino acids, such as an oligo-lysine molecule having 5 to 25 lysine moieties, an oligo-histidine molecule, or an oligo-arginine molecule, or a combined oligomer comprising any combination of histidine, arginine and lysine residues and having a total of 5 to 25 residues.

In some embodiments, nucleic acid carrier can comprise a nanoparticle or a polyplex forming agent.

In some aspects, the nucleic acid carrier can comprise a nanoparticle. The diameter of the nanoparticle can be selected to provide a sufficient size to allow transport across the cell membrane of neurons. In some embodiments, the nanoparticle can have a diameter of about 300 nm or less, or about 250 nm or less, or in a range of about 5 nm to about 250 nm, or about 10 nm to about 200 nm, or about 20 nm to about 200 nm, or about 50 nm to about 200 nm.

In accordance with inventive concepts, nanoparticles can be formed of any of the materials described as suitable nucleic acid carrier materials herein. In some embodiments, the nanoparticles carry a net positive charge. Illustrative materials for forming a nucleic acid carrier nanoparticles include, but are not limited to, amine-modified nanoparticles. In some embodiments, nanoparticles can be obtained commercially, such as those available from Phosphorex, Inc. (see Examples).

Optionally, the nucleic acid carrier comprises a polyplex forming agent. Generally, polyplexes are formed through the electrostatic interaction between negatively charged nucleic acids and cationic polymers. In some aspects, the polyplex forming agent comprises a cationic polymer, such as those described as suitable cationic nucleic acid carrier materials herein. Some preferred polyplex forming cationic polymers include, but are not limited to, polyethylenimines (PEIs), polylysine, chitosan, trimethylchitosan, and the like. Other illustrative cationic polymers useful for polyplex formation include poly(histidine), poly(D/L aspartatediethylenetriamine) (poly[Asp(DET)]), poly(ethylene glycol)-b-poly(L-lysine), PEG-b-PMPA-b-PLL, and hydrazone.

In some embodiments, nucleic acid carrier can comprise non-polymeric nucleic acid condensing agents. In accordance with these aspects, the condensing agents can comprise small, multi-charged cations that can form a complex with nucleic acid. Known condensing agents of this nature include, but are not limited to, calcium, spermine, spermidine, and the like.

Optionally, the nucleic acid carrier can comprise functional side chains for nucleic acid binding. Such functional side chains can include positively charged amines that are capable of complexing with nucleic acids. Amine groups can include primary amines, secondary amines, tertiary amines, quaternary amines, or a combination of any of these.

Optionally, the nucleic acid carrier and neural transport agent can be coupled to provide a more stable transfection reagent. The coupling of carrier and neural transport agent can occur prior or subsequent to nucleic acid loading. Optionally, the neural transport material and nucleic acid carrier material can include complementary groups to achieve such coupling. When included, such complementary groups can couple the neural transport agent and nucleic acid carrier subsequent to nucleic acid loading. In this manner, steric hindrance to nucleic acid loading of the carrier, and possible complex formation between the neural transport agent and nucleic acid carrying materials, can be reduced or circumvented.

In some embodiments, coupling of the neural transport agent and nucleic acid carrier can be accomplished by providing each component with complementary chemically reactive groups. In some embodiments, the nucleic acid carrier and the neural transport agent contain complementary bioorthagonal chemically reactive groups, such as in the Staudinger ligation. In further aspects, the nucleic acid carrier and the neural transport agent contain complementary high-affinity ligand pairs suitable for stably conjoining the moieties non-covalently. Illustrative examples include avidin-biotin and cyclodextrin-adamantane.

Optionally, nucleic acid carriers in accordance with inventive concepts can be selected to contain functionality to aid in endosome escape of nucleic acid cargo after cellular internalization. In some embodiments, inventive transfection reagents can be internalized by endocytosis, which ultimately results in localization into endosome and/or lysosome compartments. In these embodiments, the nucleic acid cargo must escape from these compartments into the cytoplasm to circumvent hydrolytic and/or enzymatic degradation of the nucleic acid cargo so that they may reach the subcellular site of activity intact, or otherwise be transported to the appropriate subcellular location such as the nucleus. In some embodiments, for example, endosomal escape can be a key step for intracellular gene and siRNA delivery. In this regard, cationic polymers with a pKa value between physiological and lysomal pH, including PEI, poly(amidoamine), poly(histidine), pAsp(DET), and the like can facilitate the endosomal escape of nucleic acid cargo.

In still further embodiments, the transfection reagent may optionally comprise a polymer, copolymer, or derivatized polymer incorporating the features of both a nucleic acid carrier and a neural transport agent. In one illustrative embodiment, a transfection reagent comprises a block copolymer, wherein a first block can provide nucleic acid carrier features, and a second block can provide neural transport agent features. In accordance with such embodiments, a nucleic acid can form a complex with the nucleic acid carrier block, and the transfection reagent can self-assemble such that the formed reagent presents a net negative surface charge. In this embodiment, a latent or chemically protected neural transport agent could be employed for transfection agent assembly, and the transport agent could be subsequently activated (prior to transfection or in situ).

The nucleic acid carrier of the transfection reagent is selected to carry a "cargo" or "payload" of nucleic acid for delivery to neuronal cells. It will be appreciated that the transfection reagents described herein can be configured to carry virtually any desired nucleic acid.

The terms "nucleic acid" and "nucleic acid molecule" can be used interchangeably herein and refer to a polymer or polymer block of nucleotides or nucleotide analogues. The nucleic acid may be obtained from natural sources, or may be produced recombinantly or by chemical synthesis. The nucleic acid can be single, double, or multiple stranded and may comprise modified or unmodified nucleotides or non-nucleotides or various mixtures and combinations thereof. Examples include: ribonucleic acid (RNA), deoxyribonucleic acid (DNA), small interfering RNA (siRNA), micro RNA (miRNA), piwi-interacting RNA (piRNA), short hairpin RNA (shRNA), antisense nucleic acid, aptamers, ribozymes, locked nucleic acid, catalytic DNA, plasmid, cosmid, artificial chromosomes, and morpholinos or other synthetic nucleic acid analogs. In some embodiments, the nucleic acid molecule can be a gene which encodes for a small interfering RNA or an aptamer, even though it does not necessarily have its more common meaning for encoding for the production of protein. The nucleic acid may be suitable for use in gene therapy, in gene vaccination or in anti-sense therapy. The nucleic acid may be or may relate to a gene that is the target for particular gene therapy or may be a molecule that can function as a gene vaccine or as an anti-sense therapeutic agent. The nucleic acid may be or correspond to a complete coding sequence or may be part of a coding sequence.

In addition to the two main components described above, inventive transfection reagents can include one or more optional components.

In some embodiments, one or more components of the transfection reagent can include functional groups. As used herein, a "functional group" or "reactive group" is a potentially reactive moiety or coupling site on a substance where one or more atoms are available for covalent coupling to some other substance. When needed, functional groups can be added to a component of the transfection reagent through derivatization or substitution reactions.

Examples of functional groups include, but are not limited to, aldehydes, allyls, amines, amides, azides, carboxyls, carbonyls, epoxys (oxiranes), ethynyls, hydroxyls, phenolic hydroxyls, phosphines, indoles, ketones, certain metals, nitrenes, perfluoroaryl groups, phosphates, propargyls, sulfhydryls, sulfonyls, vinyls, bromines, chlorines, iodines, and others. Such functional groups can be incorporated into or added to the transfection reagent components using known techniques. Where stability is desired, preferred covalent linkages can be amide bonds, peptide bonds, ether bonds, and thio ether bonds, among others.

In some embodiments, inventive transfection reagents can optionally include passivation polymer. When included, passivation polymer can passivate, "hide," and/or protect the nucleic acid carrier and cargo to enhance the stability and performance of the transfection reagent in storage and/or use. Passivation or shielding of the nucleic acid carrier/nucleic acid complex may enhance the performance of the transfection reagent, including the ability of neuronal cells to recognize and process the assembled transfection reagent as a neural transport agent. In this sense, the passivation polymer "hides" the nucleic acid carrier and its cargo in order to facilitate neuronal cell entry and transport of the transfection reagent. Passivation polymer may also decrease potential undesirable interactions between a transport agent and a carrier material disposed within, such as, for example, undesirable complex formation between a polycarboxylic acid neural transport agent outer shell and a cationic polymer-nucleic acid complex disposed within. In addition, a hydrophilic passivation polymer may facilitate assembly or self-assembly of the transfection reagent or carrier complex by virtue of its hydrophilicity.

As used herein, "passivation" is the process of making a surface "passive," that is, a surface is created that results in a reduction of biological responses when the surface is exposed to biological materials (for example, reduction of protein adsorption or reduction of cellular responses). For example, a passivating layer can form a surface having improved biological passivation as compared to material that does not include the passivator, when exposed to conditions of use (for example, in a human body). Additionally, as used herein, a passivation polymer may also function as an electrostatic shielding agent.

An illustrative example of a passivation polymer is polyethylene glycol (PEG).

In some aspects, the nucleic acid carrier or passivation polymer can include pendent amines. Such amines can provide convenient coupling sites for target ligands, as described elsewhere herein. In other aspects the nucleic acid carrier itself can be a derivative of, or copolymer comprising, a passivation polymer.

In some embodiments, the passivation polymer can include a phosphine group on the polymer terminus for covalent surface modification by Staudinger ligation. When included, the phosphine group can provide for customized conjugation of such components as neural transport agents, biomolecules and/or targeting ligands to the transfection reagent surface. The placement of reactive groups at the termini of a passivation polymer such as PEG can, in some embodiments, increase the availability of reactive groups for conjugation to other materials in solution. For example, groups for joining the carrier-cargo complex to a neural transport agent may be positioned on hydrophilic passivating polymer blocks to discourage their sequesteration when the carrier material is mixed with nucleic acid in solution.

One illustrative transfection reagent in accordance with inventive principles comprises an acrylic nanoparticle nucleic acid carrier comprising charged amine groups (which amine groups are suitable for forming a complex with a desired nucleic acid), a passivation polymer (such as PEG), the passivation polymer comprising a phosphine group for covalent attachment of a neural transport agent.

Inventive concepts further include methods of preparing transfection reagents that comprise neural transport agent and a nucleic acid carrier disposed within the neural transport agent. One of skill in the art will readily appreciate that various methods can be utilized to prepare transfection reagents, based upon the teaching herein. The particular order of assembly of the various transfection reagent components can be determined based upon principles discussed herein.

For example, in some embodiments, transfection reagents can include preformed nanoparticles as nucleic acid carriers. Suitable nanoparticles can be comprised of polymeric or copolymeric material. The preformed nanoparticles can be commercially available or prepared. In some embodiments, nanoparticles having a desired diameter can be prepared by nanoprecipitation of a selected polymeric or copolymeric carrier.

In one embodiment, nanoparticles can be prepared by nanoprecipitation. Typically, 20 mg of selected polymeric carrier is dissolved in 4 ml acetone or THF, and the solution is added, with magnetic stirring, to 8 ml distilled water (DI $H_2O$). Precipitation of particles occurs spontaneously. After solvent evaporation under reduced pressure, an aqueous suspension of nanoparticles (approximately 2.5 mg/ml) is obtained. The particles can then be filtered through a 1.2 μm filter (Millext AP, Millipore) and stored at 4° C. until use.

In other embodiments, insoluble polyplex nanoparticles can be formed from solution upon incubation of soluble nucleic acid carrier material(s) with soluble nucleic acid. Such complexes can be prepared in aqueous solution by mixing plasmid DNA with nanoparticle suspension at different concentrations (N/P ratios in the range of about 0.5 to 60). The complexes are incubated at room temperature for a suitable time (for example, 30 minutes).

The diameter of the nanoparticle or polyplex can be selected to provide a sufficient size for transport across the cell membrane of neurons. In some aspects, the nanoparticle or polyplex can have a diameter of about 300 nm or less, or about 250 nm or less, or in a range of about 5 nm to about 250 nm, or about 10 nm to about 200 nm, or about 20 nm to about 200 nm, or about 50 nm to about 200 nm.

One illustrative method of preparing a transfection reagent is as follows. The transfection reagent in accordance with this embodiment comprises cationic cyanoacrylate copolymer nanoparticles as nucleic acid carrier. A cationic cyanoacrylate copolymer containing pendent PEG chains, which terminate in reactive groups (such as azido- or phosphine groups), is utilized to prepare nucleic acid carrier nanoparticles by dissolving the cyanoacrylate copolymer in solvent, and the solution is added, with stirring, to deionized $H_2O$. Precipitation occurs spontaneously. After solvent evaporation under reduced pressure, an aqueous suspension of nanoparticles is obtained. Nanoparticles are filtered and stored until use. Nucleic acids can be condensed onto the preformed nanoparticles by electrostatic interaction (via interaction with the cationic copolymer portion of the nucleic acid carrier material). Nanoparticle complexes are prepared in aqueous solution by mixing nucleic acid with nanoparticle suspension at the selected N/P ratio. Complexes are incubated at room temperature.

Subsequently, a neural transport agent containing a complementary reactive group can be conjugated to the nanoparticle or polyplex surface through chemical ligation. This conjugation can take place via the reactive groups of the nucleic acid carrier (for example, azido- or phosphine) and the complementary reactive groups of the neural transport agent. For example, the azido-ligand or phosphine nanoparticles can be suspended in PBS at desired concentrations. The Staudinger ligation is allowed to proceed for 8 hours at room temperature, and final product is purified by dialysis. The resulting transfection reagent comprises neural transport agent conjugated to nucleic acid carrier, wherein the nucleic acid carrier comprises nanoparticles formed of a cationic cyanoacrylate copolymer containing pendent PEG chains. In this embodiment, the transfection reagent comprises PEG as a passivation polymer.

Combination of the nucleic acid carrier and the neural transport agent can be performed prior to, or after, incorporation of nucleic acid to be carried by the transfection reagent. In some embodiments, the nanoparticulate or polyplex-forming nucleic acid carrier materials can each comprise neural transport moieties prior to nucleic acid complex formation. For example, preformed nanoparticles can result from nano-precipitation of a block copolymer that comprises a neural transport moiety, or preformed nanoparticles may undergo subsequent surface modification to incorporate a neural transport agent prior to nucleic acid loading. Similarly, a polyplex forming carrier material may comprise a neural transport moiety in a soluble copolymer or be prejoined with a neural transport agent prior to polyplex formation.

Alternatively, it can be preferable in some embodiments to complex the nucleic acid carrier and its cargo nucleic acid prior to addition of a neural transport agent. For example, these embodiments may reduce the potential for steric hindrance towards nucleic acid loading which may result from surface-resident neural transport agent (as, for example, in the case of preformed nanoparticulate carriers) or undesirable interactions of the carrier material or nucleic acid molecules with the neural transport agent, which may impede proper assembly of the transfection reagent (as, for example, in the case of a polyplex forming copolymer containing a cationic block to carry nucleic acids and an anionic neural transport agent block).

In like manner, passivation polymer (when included) can be added to the transfection reagent either prior to or after nucleic acid complex formation, as desired.

The transfection reagents can further comprise any additional desired components, including, for example, glucose, a buffer, a lipid, an additional nucleic acid, an additional polymer, a proteinaceous composition, a polysaccharide, an endosome agent, a targeting agent, a pharmaceutical carrier, or a combination of any two or more of these.

As discussed herein, the particular order of assembly of the transfection reagent components (nucleic acid carrier, neural transport agent, and optional components, when desired) is not critical. Once formed, the transfection reagent comprises a nucleic acid carrier disposed within the neural transport agent. The overall size of the formed transfection reagent is suitable for neuronal uptake. Illustrative transfection reagents can have an overall effective diameter of 300 nm or less, or 250 nm or less, or 200 nm or less; for example, about 5 nm to about 250 nm, or about 5 nm to about 200 nm, or about 10 nm to about 200 nm, or about 10 nm to about 150 nm, or about 10 nm to about 100 nm. For purposes of the present discussion, the overall effective diameter of the transfection reagent is the average diameter of a spherical reagent which will give identical (or nearly identical) geometric behavior to that of the reagent (which may be nonspherical) being examined. The geometric behavior includes the ability of the reagent to cross neuronal membranes.

In further aspects, a composition for transfection of neuronal cells is provided, the composition comprising at least one transfection reagent as described herein, wherein the transfection reagent is either in solution or has been lyophilized. Such compositions can be used as "kits" for preparation of transfection reagents by an end user. In some aspects, the end user can select one or more nucleic acid(s) to include in the transfection reagent, and/or one or more targeting ligand(s). In accordance with these various aspects, customizable transfection reagents can be provided.

In other embodiments, the transfection reagent can be provided as a composition (for example, a kit) that includes one or more of its components as separate constituents that are combined by an end user. For example, a transfection composition can be provided that includes neural transport agent and nucleic acid carrier as separate components, wherein each component is provided in solution or has been lyophilized (either independently or in combination). An end user can then select a desired nucleic acid and prepare a customized transfection reagent in accordance with principles described herein. Optionally, transfection compositions can include instructions for combining individual components (neural transport agent, nucleic acid carrier, and/or nucleic acid).

Suitable solvents can be selected based upon known principles. For example, when individual components of the transfection reagent are provided separately, suitable solvent can be selected for each individual component. Suitable solvents for neural transport agents described herein are generally known. Some neural transport agents are water soluble (for example Diamidino Yellow), while other transport agents may require organic solvents. Optionally, suspensions of insoluble dyes can be sonicated and/or filtered.

In yet further aspects, there are provided methods of transfecting neuronal cells. In one embodiment, a method for transfecting a neuronal cell comprises steps of (a) providing a transfection reagent comprising (1) a neural transport agent and (2) a nucleic acid carrier complexed with nucleic acid and disposed within the neural transport agent, and (b) exposing a cell or tissue to the transfection reagent.

In some embodiments, transfection can be performed in vitro in cultured hippocampal neurons. Neurons can be isolated form the hippocampus of postnatal day 1-2 Sprague Dawley rats, according to known procedures. Neurons can be grown in Neurobasal A (Invitrogen), supplemented with B27 (Invitrogen) and Glutamax (Invitrogen) for up to 21 days in vitro. Cultured hippocampal neurons can be transfected at various time points ranging from 1-21 days or more in vitro. Transfection incubations are performed at 37° C.

In some embodiments, the transfection reagent is exposed to cultured neurons or cultured tissue by supplementation of the cell culture growth media. Alternatively, transfection reagents are injected into the body of a human or non-human animal such that neurons of the central or peripheral nervous system are exposed (for example stereotaxic injection, lumbar puncture, and parenteral administration). Transfection reagents can also be administered by topical application, particularly where a wound, sore, or blister may be present. Additional embodiments include, for example, ocular, transscleral, transcochlear, transdermal and oral delivery routes as well as insufflation and inhalation. In accordance with inventive methods, transfection efficiency towards desired target cells can be greater than about 30% or 40% or 50% or 60% or 70% or 80% or 90%.

The neuronal exposure step can produce expression of an RNA encoded by the nucleic acid subsequent to internalization of the transfection reagent. However, any nucleic acid could potentially be delivered in accordance with inventive principles, whether the nucleic acid includes a coding sequence or not.

In further embodiments, transfection can be performed in vivo by injection of transfection reagent to a desired site, using known stereotaxic surgical procedures.

Inventive concepts further provide processes for expressing a nucleic acid in host cells, which comprises contacting the host cells in vitro or in vivo with a transfection reagent of the invention comprising the nucleic acid and then culturing the host cells under conditions that enable the cells to express the nucleic acid. In cases in which the host cells are contacted in vivo, methods include the step of allowing the host cells to express the nucleic acid within the body.

Inventive concepts further provide processes for production of a protein in host cells, which comprises contacting host cells in vitro or in vivo with a transfection reagent of the invention that comprises a nucleic acid that encodes the protein, allowing the cells to express the protein. Methods can further comprise a step of obtaining the expressed protein. The protein may be obtained either from the host cell or from the culture medium.

Inventive concepts further provide methods of transfecting cells comprising subjecting the cells to a transfection reagent according to the invention.

Inventive concepts further provide cells, transfected with a nucleic acid by a method according to the invention, and also progeny of such cells.

Inventive concepts further provide a disease model for use in testing candidate pharmaceutical agents, which comprises cells transfected by a method according to the invention with a nucleic acid suitable for creating the disease model.

Inventive concepts further provide a pharmaceutical composition which comprises a transfection reagent of the invention comprising a nucleic acid in admixture or in conjunction with a pharmaceutically suitable carrier. The composition may be a vaccine.

Inventive concepts also provide methods for therapeutic manipulation of neuronal activity, neuronal plasticity, or synaptic plasticity.

Inventive concepts also provide methods for introduction of optogenetic material to neurons or synaptic networks.

Inventive concepts further provide methods for the treatment or prophylaxis of a condition caused in a human or in a non-human animal by a defect and/or a deficiency in a gene, which comprises administering to the human or the non-human animal a transfection reagent of the invention comprising a nucleic acid suitable for correcting the defect or deficiency.

Inventive concepts also provide methods for therapeutic or prophylactic immunization of a human or of a non-human animal, which comprises administering to the human or to the non-human animal a transfection reagent in accordance with inventive concepts comprising an appropriate nucleic acid.

Inventive concepts further provide methods of anti-sense therapy of a human or non-human animal, comprising administering to the human or non-human animal a transfection reagent comprising anti-sense nucleic acid.

Inventive concepts further provide the use of a transfection reagent of the invention comprising a nucleic acid for the manufacture of a medicament for the prophylaxis of a condition caused in a human or in a non-human animal by a defect and/or a deficiency in a gene, for therapeutic or prophylactic immunization of a human or of a non-human animal, or for anti-sense therapy of a human or of a non-human animal.

The nucleic acid is administered in an amount effective for its intended purpose.

The treatments and uses described herein can be carried out by administering the respective transfection reagent or medicament in an appropriate manner, for example, administration may be accomplished by injection to the site of treatment.

In a further embodiment, inventive concepts provide a kit comprising a transfection reagent comprising a nucleic acid.

Inventive concepts also provide kits that comprise the following items: (a) a neural transport agent; and (b) a nucleic acid carrier selected to complex with a nucleic acid of interest, wherein the neural transport agent comprises a synthetic polymer having a net negative charge under mammalian physiological conditions. Such kits may further comprise (c) nucleic acid. Such a nucleic acid may be single-stranded or double stranded and may be a plasmid or an artificial chromosome. The nucleic acid component may be provided by a vector complex suitable for the expression of the nucleic acid, the vector complex being either empty or comprising the nucleic acid. For in vivo treatment purposes, the nucleic acid may comprise DNA appropriate for the correction or supplementation being carried out. Such DNA may be a gene, including any suitable control elements, or it may be a nucleic acid with homologous recombination sequences.

A kit generally comprises instructions, which preferably indicate the preferred ratios of the components and the preferred order of use or admixing of the components, for example, as described herein. A kit may be used for gene therapy, gene vaccination or anti-sense therapy.

Transfection reagents, methods and compositions described herein can possess utility as research tools, imaging tools, diagnostic agents, and therapeutic agents, for example.

Illustrative therapeutic applications include as gene therapies. In some aspects, the simplicity of the delivery composition allows the use of any type or size of therapeutic genetic constructs to be delivered. Illustrative neurological diseases and disorders that may be treated include, but are not limited to, chronic maladaptive or pathologic neural plasticity (such as addiction, epilepsy, post-traumatic stress disorder, stroke), traumatic brain injury, cognitive disorders, and chronic pain. Inventive transfection reagents may also be useful in the therapeutic treatment for Herpes lesions at peripheral sensory nerve endings (for example, suppression of Herpes simplex or Herpes Zoster virulence genes).

The following example is representative of embodiments of the present invention and is not intended to be exhaustive. The example is not to be taken as limiting the scope of the invention but rather so that others skilled in the art can appreciate practices of the present invention. Unless otherwise noted, all percentages are by weight.

EXAMPLES

Example 1

Neuronal Uptake of Cationic Nanoparticles Disposed within a Neural Transport Agent Conventional transfection reagents are not efficient at transfecting mature neurons. Typically, transfection reagents comprise a cationic carrier molecule, for example PEI or DOTAP, complexed with nucleic acid in nanoparticulate form. Such nanoparticles do not efficiently cross the plasma membrane of mature neurons, which is a necessary step for nucleic acid transfection. The following experiment was performed to investigate the effect of modifying the surface chemistry of a cationic carrier nanoparticle.

Rhodamine-labeled, amine-functionalized polystyrene nanoparticles (100 nm diameter) were obtained from Phosphorex, Inc. (Fall River, Mass., "Fluorophorex," product #2221-01). These cationic nanoparticles are a styrene and amine co-polymer (5% of the repeating units contain pendent primary amines). The nanoparticle surface chemistry was covalently modified with polyacrylic acid (5000 g/mol, Aldrich) using the EDC (Life Technologies) coupling method. The following conditions were investigated:

Four reactions were run. A 200 µL suspension of Fluorophorex was used for each reaction. Each 200 µL sample of Fluorophorex was diluted to 1 mL with aqueous MES buffer (50 mM), pH 4.5, and protected from light.
1) 200 µL Fluorophorex (2 mg)+1 mg PAA (sigma, MW 5000 g/mol)+1 mg EDC
2) 200 µL Fluorophorex (2 mg)+3 mg PAA+3 mg EDC
3) 200 µL Fluorophorex (2 mg)+3 mg PAA+10 mg EDC
4) 200 µL Fluorophorex (2 mg)+3 mg PAA (no EDC)

The four solutions were prepared fresh and the mixtures were immediately vortexed for 10 seconds on high after near simultaneous addition of EDC and PAA. Upon addition of PAA (sodium salt of) and EDC, the solution pH was approximately 5.5. The conjugation reactions were allowed to proceed for 45 minutes at room temperature in the dark, and then placed at 4° C. overnight. Nanoparticle suspensions remained stable in solution, except in the case of reaction 4, which resulted in the precipitation of the majority of the nanoparticles.

The prepared formulations were then purified by dialysis, concentrated using an amicon centrifugal filter (5000 NMWL cutoff), and resuspended in cell culture grade water (Hyclone High-Pure) at 2 mg/ml. The purified products were compared to unmodified Fluorophorex and conventional transfection with Lipofectamine 2000™ (pEGFP expression), in their abilities to label neuronal soma in mature cultures of dissociated striatal neurons. The experiments were performed in 15 day old (days in vitro) primary rat striatal neurons and compared to pEGFP transfection using Lipofactamine 2000™ according to its manufacturer's protocol (Life Technologies, CA). Rat striatal cultures were prepared on postnatal day zero and cultured in the presence of ARA-C (or 1-beta-d-arabinofuranosyl-cytosine, cytarabine), to select for neuronal populations, in 24-well TCPS plates coated with polylysine. Cell cultures were maintained at 37° C. in a $CO_2$ (5%) incubator, and fed with MEM (supplemented with Gentamycin, transferrin, insulin, B27, Glutamax™, and 5% serum). Under these conditions, medium spiny neurons/principal neurons predominated the cultures. Nanoparticle incubation with neurons was done in the presence of 5% serum without changing the standard growth media. In the experiments shown, 20 µL of a 2 mg/mL nanoparticle suspension in deionized water was added to the respective wells in a 24-well plate (1 mL growth media/well). Brightfield and fluorescence microscopy was utilized to determine cellular uptake of the nanoparticles and expression of EGFP (FIG. 1).

As illustrated in FIG. 1, neural transport surface chemistry induced robust handling of cationic nanoparticles by mature cultured neurons (15 days in vitro, Rat). In the Figure, Brightfield image and corresponding fluorescence images are shown side by side. FIG. 1A illustrates unmodified amine nanoparticles; FIG. 1B illustrates amine nanoparticles mixed with PAA (reaction 4); FIG. 1C illustrates amine nanoparticles conjugated to PAA (reaction 2); and FIG. 1D illustrates Lipofectamine 2000™/pEGFP transfection.

As shown in FIG. 1A, fluorescent cationic nanoparticles (which did not contain neural transport agent) produced faint background staining and extracellular aggregation that did not correspond to labeling of neuronal processes or soma. In FIG. 1B, incubation of fluorescent cationic nanoparticles with anionic polyacrylic acid in the absence of EDC (without conjugating the nanoparticles to the polyacrylic acid) did not result in neuronal labeling. In FIG. 1C, neuronal uptake and retrograde transport of fluorescent, cationic nanoparticles covalently surface-modified with polyacrylic acid was observed, resulting in efficient labeling of neuronal soma. FIG. 1D illustrates conventional low-efficiency transfection of pEGFP using Lipfectamine 2000™ observed in this Example.

These results demonstrated that polyanionic surface chemistry induced uptake and retrograde transport of cationic nanoparticles in mature neurons, resulting in their efficient labeling.

Example 2

Neuronal Uptake of Cationic Nanoparticles Disposed within a Neural Transport Agent The surface chemistry of cationic nanoparticles was stably modified with horseradish peroxidase as neural transport agent, and the nanoparticle/HRP conjugate was introduced into neuronal cells as follows.

Fluorescent cationic nanoparticles (100 nm diameter polystyrene with 5 mole % pendent primary amine, 1% wt/vol in water) were obtained from Phosphorex, inc. (Fall River, Mass., "Fluorophorex," product #2221-01). The nanoparticles were dialyzed (100 k molecular weight cut-off membrane) into PBS, pH 7.4, and diluted 5 fold for biotinylation (Sulfo-NHS-LC-Biotin, Thermo Fisher Scientific, Inc., Rockford Ill.).

Biotinylation reactions were carried out at room temperature in PBS, pH 7.4 for 45 minutes in the dark. The reaction was carried out over a range of 300 µM to 300 nM biotinylation reagent (range of 50,000, 5000, 500 or 50 molecules of sulfo-NHS-LC-biotin per nanoparticle). It was observed that above 3000 nM biotinylation reagent (500:1), nanoparticles tended to form stable aggregates and did not lead to neuronal labeling following conjugation to HRP, presumably due to their larger size. Probe sonication was not effective to disrupt this nanoparticle aggregation.

Following biotinylation, the nanoparticle suspensions were dialyzed again (as described above) with PBS and conjugated to the neural transport protein horseradish peroxidase (HRP), as follows. HRP-streptavidin conjugate was purchased from Rockland Immunochemicals (Gilbertsville, Pa.) and incubated with biotinylated fluorescent nanoparticles. HRP-streptavidin conjugate was dissolved in PBS (pH 7.4) at a concentration of 5 mg/mL to create a stock solution, which was then added to the biotinylated nanoparticle suspensions at a final concentration of 1 mg/mL. The suspensions were incubated in the presence of HRP-streptavidin for 3 hours in the dark, and once again dialyzed with PBS (as described above). The interaction between biotin and avidin is highly specific and considered essentially irreversible (similar to a covalent bond).

The nanoparticle/HRP conjugates were introduced into neuronal cells as follows. Dissociated hippocampal cultures were prepared from P1 rats (Sprague Dawley) and cultured in the presence of ARA-C to select for a purely neuronal population (predominantly projection neurons and interneurons). Cultures were maintained at 37° C. in a $CO_2$ (5%) incubator, and fed with Neurobasal A media supplemented with B-27 and Glutamax™. Purified suspensions of the nanoparticle/HRP conjugates, in amounts of 10 or 80 µL, were added to cultured hippocampal neurons (day 14 in vitro, 24-well plates containing poly-L-lysine-coated glass coverslips) to measure fluorescent labeling of neuronal cytoplasm. Incubations were performed at 37° C. for 24 hours before visualization.

Brightfield and fluorescence microscopy were utilized to determine cellular uptake of fluorescent cationic nanoparticles, with and without conjugation to neural transport agent. Unmodified nanoparticles, biontinylated nanoparticles, and streptavidin-conjugated biotinylated nanoparticles were used as separate negative controls.

Figure 2:
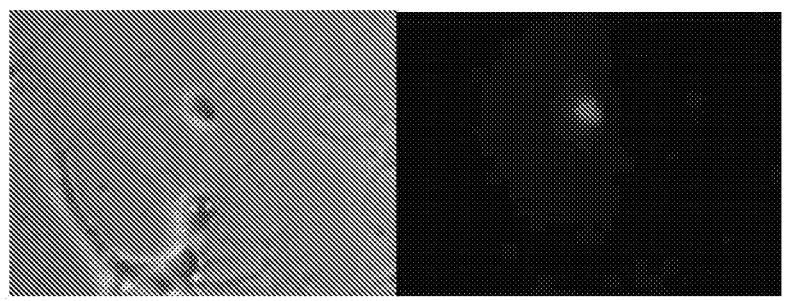
FIG. 2 illustrates brightfield image and corresponding fluorescence image of mature cultured neurons including cationic nanoparticle/horseradish peroxidase conjugates introduced into mature neurons in accordance with inventive aspects.
Figure 2:
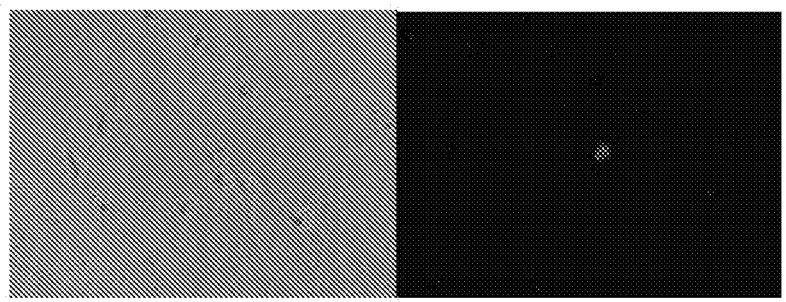
Figure 2:
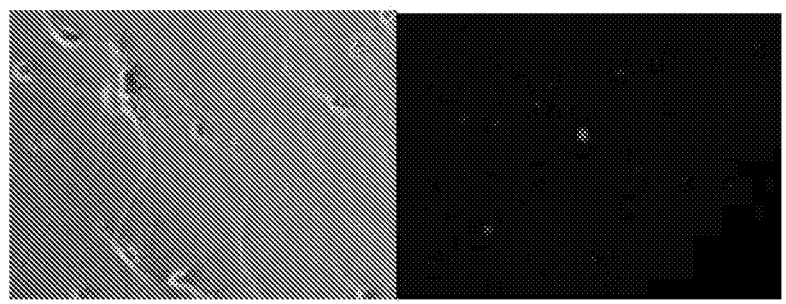
Figure 2:
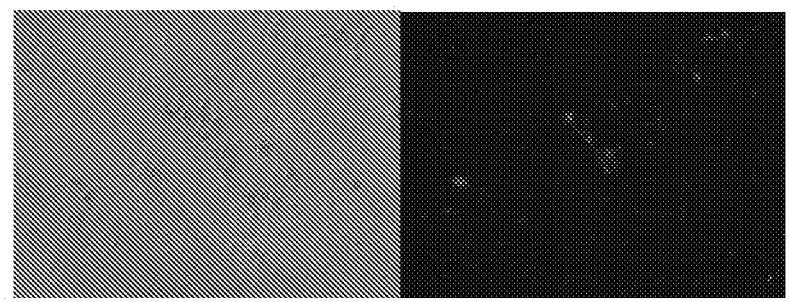

Results are illustrated in FIG. 2. As shown, HRP effectively masked cationic nanoparticles and induced its cellular uptake by developmentally mature neurons. Results further indicated that none of the negative controls (including cationic nanoparticles that did not include HRP) produced any detectable labeling of neuronal cytoplasm (data not shown).

FIG. 2 shows Brightfield and corresponding fluorescence images of neurons labeled with HRP-conjugated fluorescent cationic nanoparticles, approximately 24 hours following their addition to the culture media. FIG. 2 illustrates examples of neuronal soma labeled by fluorescent cationic (primary amine) nanoparticles conjugated to HRP at a theoretical ratio of 50 molecules per nanoparticle. To induce neuronal labeling, 10 µL (A) or 80 µL (B) of a 1 mg/mL nanoparticle suspension was added to the standard growth media (1 mL). The higher dose used in B resulted in some observable extracellular particle aggregates; however punctuate staining of the proximal dendrites, in addition to the soma, can be seen for the neuron in the center of the image.

Results shown in FIGS. 1 and 2 strongly support the intracellular delivery of cationic nucleic acid carrier materials to developmentally mature neurons, when in nanoparticle or condensed form and disposed within a neural transport agent.

Example 3

Nucleic Acid Transfection of Developmentally Mature Neurons Via Surface Modification of Polyplex with a Neural Transport Agent Phosphine-functionalized polyplex and azido-functionalized polyacrylic acid (PAA) were prepared prior to their conjugation. To prepare functionalized polyplex, Chitosan (Novafect G 214, glutamate salt, >90% deacetylated chitin) was purchased from Novamatrix (Sandvika, Norway), and complexed with pCAG-EGFP (Clontech, Otsu, Japan) in ultrapure water at a charge ratio of 4:1 (nitrogen:phosphate), according to the manufacturer's directions. The polyplex was then purified by size exclusion chromatography, exchanging the polyplex into phosphate buffered saline (PBS), pH 7.4. The polyplex was then modified with sulfo-NHS-phosphine (Thermo Fisher Scientific, Rockford, Ill.) for 30 minutes in the dark at 22° C., and repurified by size exclusion chromatography. The mole ratio of phosphine to chitosan in the coupling reaction was estimated to be 5:1.

PAA (5000 g/mol, Sigma Aldrich, Saint Louis, Mo.) was modified with amino-PEG-azide (11-Azido-3,6,9-trioxaundecan-1-amine, Sigma Aldrich) using an EDC coupling reaction, purified, and lyophilized. The EDC coupling reaction utilized amino-PEG-azide as the limiting reagent, and was performed at a 5:1 mol ratio of azide to PAA.

The phosphine-functionalized polyplex was disposed within azido-PEG-PAA through Staudinger ligation for 3.5 hours at 37° C. in the dark. The azide of PAA was equimolar to phosphine in PBS, pH 7.4, during the coupling reaction.

Rat hippocampal cultures were prepared on postnatal day one and cultured without serum in Neurobasal Media (Life Technologies), supplemented with B-27, Glutamax™ and ARA-C. ARA-C kills dividing cells, thus enabling the culture of a pure neuronal population. Neurons were seeded at 75,000 cells per well in 24-well TCPS plates coated with polylysine. Neuronal cultures were maintained at 37° C. in a $CO_2$ (5%) incubator.

For nucleic acid transfection, the PAA-modified chitosan-pEGFP polyplex was utilized as follows. Transfection was performed in 10 d.i.v. (days in vitro) primary rat hippocampal neurons. Transfection was initiated by the addition of 1004 PAA-conjugated polyplex (in PBS, ~1 µg DNA/well) to the growth media (800-900 µL/well). Fluorescence microscopy was utilized to detect the expression of EGFP protein (FIG. 3) in the culture.

Figure 3:
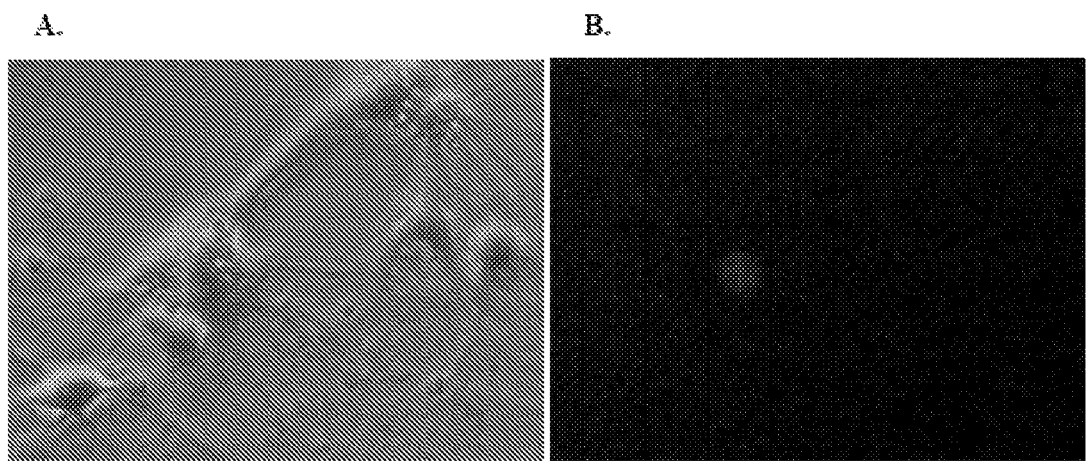
FIG. 3 illustrates brightfield image and corresponding fluorescence image of mature cultured neuron transfected with transfection reagent in accordance with inventive aspects.

FIG. 3 illustrates a neuron transfected with chitosan-pEGFP polyplex, having been disposed within a shell of poly(acrylic acid) through Staudinger ligation. These results demonstrate that a nucleic acid carrier material, when complexed with a nucleic acid and disposed within a polyanionic surface chemistry, can lead to the successful transfection of mature neurons. Perinuclear expression of eGFP protein (FIG. 3B, fluorescence image) can be seen for the larger neuron just left of center (FIG. 3A, brightfield image). Results showed no fluorescent neurons could be found in parallel control experiments, which utilized the same batch of chitosan:DNA polyplex, but without subsequent modification.

What is claimed is:

1. A transfection reagent comprising
   (a) a neural transport agent comprising an enzyme, polymer, lectin, fluorescent dye, dextran, or a combination of any two or more of these, and
   (b) a nucleic acid carrier disposed within and conjugated to the neural transport agent,
   wherein the nucleic acid carrier and the neural transport agent comprise complementary chemically reactive groups or high affinity ligands to conjugate the carrier and the transport agent, and
   wherein the transfection reagent has a net negative surface charge under mammalian physiological conditions and an overall effective diameter of 5 to 250 nm.

2. The transfection reagent according to claim 1, wherein the neural transport agent comprises a polycarboxylic acid.

3. The transfection reagent according to claim 1, wherein the neural transport agent comprises an acrylic polymer.

4. The transfection reagent according to claim 3, wherein the neural transport agent comprises poly(acrylic acid) or poly(methacrylic acid).

5. The transfection reagent according to claim 1, wherein the nucleic acid carrier contains amines.

6. The transfection reagent according to claim 1, wherein the transfection reagent additionally comprises a neuronal cell subtype targeting ligand.

7. The transfection reagent according to claim 1, wherein the nucleic acid carrier is a nanoparticle whose diameter is in a range of 5 nm to 250 nm.

8. The transfection reagent according to claim 1, wherein the nucleic acid carrier comprises a polyplex forming agent.

9. The transfection reagent according to claim 1, wherein the nucleic acid carrier comprises a cationic polymer.

10. The transfection reagent according to claim 1 further comprising nucleic acid.

11. The transfection reagent according to claim 10, wherein the nucleic acid is selected from RNA, DNA, siRNA, miRNA, piRNA, shRNA, antisense nucleic acid, aptamers, ribozymes, locked nucleic acid, catalytic DNA, plasmid, cosmid, artificial chromosomes, morpholinos or other synthetic nucleic acid analogs.

12. The transfection reagent according to claim 1 further comprising a passivating polymer.

13. A composition for transfection of neurons, the composition comprising a neural transport agent comprising an enzyme, polymer, lectin, fluorescent dye, dextran, or a combination of any two or more of these and a nucleic acid carrier, wherein the neural transport agent and the nucleic acid carrier are conjugated to each other via complementary chemically reactive groups or high affinity ligands, and wherein, once conjugated, the composition has a net negative surface charge under mammalian physiological conditions and an overall effective diameter of 5 to 250 nm or less.

14. The composition according to claim 13, further comprising nucleic acid.

15. The composition according to claim 13, wherein the neural transport agent and the nucleic acid carrier are separate but capable of forming a stable interaction when mixed together.

16. The transfection reagent according to claim 1, wherein the nucleic acid carrier and the neural transport agent contain complementary bioorthagonal chemically reactive groups.

* * * * *